(12) United States Patent
Grootaert et al.

(10) Patent No.: US 7,294,677 B2
(45) Date of Patent: Nov. 13, 2007

(54) CATALYST FOR MAKING FLUOROELASTOMER COMPOSITIONS AND METHODS OF USING THE SAME

(75) Inventors: Werner M. A. Grootaert, Oakdale, MN (US); Miguel A. Guerra, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 253 days.

(21) Appl. No.: 11/211,884

(22) Filed: Aug. 25, 2005

(65) Prior Publication Data

US 2007/0049698 A1 Mar. 1, 2007

(51) Int. Cl.
*C08F 8/18* (2006.01)

(52) U.S. Cl. .............................. 525/326.3; 525/326.4; 525/359.3

(58) Field of Classification Search ............. 525/326.3, 525/326.4, 359.3
See application file for complete search history.

(56) References Cited

U.S. PATENT DOCUMENTS

| | | | |
|---|---|---|---|
| 4,281,092 A | 7/1981 | Breazeale | |
| 4,886,862 A * | 12/1989 | Kuwamura et al. | ......... 526/247 |
| 5,545,693 A | 8/1996 | Hung et al. | |
| 5,565,512 A | 10/1996 | Saito et al. | |
| 5,621,145 A | 4/1997 | Saito et al. | |
| 5,637,648 A | 6/1997 | Saito et al. | |
| 5,668,221 A | 9/1997 | Saito et al. | |
| 5,700,879 A | 12/1997 | Yamamoto et al. | |
| 5,767,204 A | 6/1998 | Iwa et al. | |
| 6,255,536 B1 | 7/2001 | Worm et al. | |
| 6,281,296 B1 | 8/2001 | McLachlan et al. | |
| 6,294,627 B1 | 9/2001 | Worm et al. | |
| 6,482,979 B1 | 11/2002 | Hintzer et al. | |
| 6,657,012 B2 | 12/2003 | Grootaert et al. | |
| 6,657,013 B2 | 12/2003 | Grootaert et al. | |
| 6,794,457 B2 | 9/2004 | Grootaert et al. | |
| 6,803,425 B2 | 10/2004 | Hintzer et al. | |
| 6,844,388 B2 | 1/2005 | Grootaert et al. | |
| 6,846,880 B2 | 1/2005 | Grootaert et al. | |
| 6,890,995 B2 | 5/2005 | Kolb et al. | |
| 2004/0162395 A1 | 8/2004 | Grootaert et al. | |
| 2005/0154145 A1 * | 7/2005 | Kolb et al. | ............... 525/326.3 |
| 2006/0135827 A1 * | 6/2006 | Grootaert et al. | ........... 570/123 |

OTHER PUBLICATIONS

Farah et al., "Perhalo Ketones. V. The Reaction of Perhaloacetones with Aromatic Hydrocarbons", J. Org. Chem., 1965, vol. 30, pp. 998-1001.
ASTM: D 1646-04, Standard Test Methods for Rubber-Viscosity, Stress Relaxation, and Pre-Vulcanization Characteristics (Mooney Viscometer), pp. 1-12.
Grootaert et al., "Curing Compositions for Fluoropolymers", U.S. Appl. No. 11/014,042, filed Dec. 16, 2004.

* cited by examiner

*Primary Examiner*—Bernard Lipman
(74) *Attorney, Agent, or Firm*—Dena M. Ehrich; C. Michael Geise (57) ABSTRACT

A catalyst is preparable from a first component represented by $R'C(CF_2R)O^-Q^+$ and a second component $(NCCFR'')_bZ$. The catalyst may be combined with a fluoropolymer having nitrogen-containing cure-sites to form a curable composition that is useful for preparing fluoroelastomer compositions.

32 Claims, 1 Drawing Sheet

FIG. 1

CATALYST FOR MAKING FLUOROELASTOMER COMPOSITIONS AND METHODS OF USING THE SAME

BACKGROUND

Fluoroelastomer compositions are particularly useful as seals, gaskets, and molded parts in systems that are exposed to elevated temperatures and/or corrosive materials. For sealing applications that require resistance to the most extreme conditions, perfluorinated elastomers are used. Such parts are used in applications such as automotive, chemical processing, semiconductor, aerospace, and petroleum industries, among others.

Curable compositions used to make fluoroelastomer compositions often include a fluoropolymer comprising monomer units having a nitrogen-containing cure site to facilitate cure in the presence of a curative. One class of useful cure-site components used in fluoroelastomers includes nitrogen-containing groups such as, for example, nitrites and imidates.

Fluoroelastomer compositions are typically prepared by combining a fluoropolymer resin or gum (sometimes referred to in the art as a fluoroelastomer gum) with one or more curatives to form a curable composition, shaping the curable mixture into a desired shape, and then curing the curable composition until the desired physical properties are achieved. During mixing of the curative(s) and fluoropolymer resin, and in subsequent handling prior to the curing step, the curable mixture may undergo a degree of premature curing (sometimes referred to in the art as incipient curing) that renders the curable composition difficult or impossible to shape. This premature curing is typically accompanied by a viscosity increase, and is referred to in the elastomer curing art as "scorch". Typically, scorch is reported with reference to "Mooney scorch" which is a measure of the incipient curing characteristics of a rubber compound using the Mooney viscometer. Mooney scorch is typically determined according to a standard test method such as, for example, ASTM D1646-04 "Standard Test Methods for Rubber-Viscosity, Stress Relaxation, and Pre-Vulcanization Characteristics (Mooney Viscometer)".

In general, the lower the degree of observed scorch, the greater will be the processing window during manufacture of shaped fluoroelastomer articles.

SUMMARY

In one aspect, the present invention provides a method of making a fluoroelastomer composition, the method comprising sequentially:

(a) providing a reaction product of first and second compositions, wherein the first composition comprises a first component represented by Formula I:

wherein $Q^+$ is a non-interfering organophosphonium, organosulfonium, or organoammonium cation;

each R independently represents H, halogen, a hydrocarbyl group or a halogenated hydrocarbyl group, wherein at least one carbon atom of the hydrocarbyl group may be further substituted with one or more heteroatoms selected from N, O and S;

R' represents H, a hydrocarbyl group, or a halogenated hydrocarbyl group, wherein at least one carbon atom of the hydrocarbyl group may be further substituted with one or more heteroatoms selected from N, O and S;

or any two of R and R' may together form a divalent hydrocarbylene group, wherein at least one carbon atom of the hydrocarbylene group may be further substituted by one or more heteroatoms selected from N, O and S; and the second composition comprises a second component represented by Formula II:

wherein each R" independently represents F or $CF_3$;

b represents any positive integer;

Z represents a b-valent organic moiety free of interfering groups; and (b) combining the reaction product from step (a) with at least one component comprising a fluoropolymer to form a curable composition, the fluoropolymer comprising at least one interpolymerized monomer unit having a nitrogen-containing cure site; and (c) at least partially curing the curable composition to form a fluoroelastomer.

In another aspect, the present invention provides a curable composition comprising:

(a) first and second components, or a reaction product thereof, wherein the first component is represented by Formula I:

wherein $Q^+$ is a non-interfering organophosphonium, organosulfonium, or organoammonium cation;

each R independently represents H, halogen, a hydrocarbyl group or a halogenated hydrocarbyl group, wherein at least one carbon atom of the hydrocarbyl group may be further substituted with one or more heteroatoms selected from N, O and S;

R' represents H, a hydrocarbyl group, or a halogenated hydrocarbyl group, wherein at least one carbon atom of the hydrocarbyl group may be further substituted with one or more heteroatoms selected from N, O and S;

or any two of R and R' may together form a divalent hydrocarbylene group, wherein at least one carbon atom of the hydrocarbylene group may be further substituted by one or more heteroatoms selected from N, O and S; and the second component is represented by Formula II:

wherein
each R" independently represents F or $CF_3$;
b represents any positive integer;
Z represents a b-valent organic moiety free of interfering groups, and wherein neither of the first and second components are fluoropolymers that comprise an interpolymerized monomer unit having a nitrogen-containing cure site; and (b) a fluoropolymer comprising at least one interpolymerized monomer unit having a nitrogen-containing cure site.

In yet another aspect, the present invention provides catalyst composition preparable by reaction of components comprising:

(a) a first component represented by Formula I:

wherein
Q+ is a non-interfering organophosphonium, organosulfonium, or organoammonium cation, each R independently represents H, halogen, a hydrocarbyl group or a halogenated hydrocarbyl group, wherein at least one carbon atom of the hydrocarbyl group may be further substituted with one or more heteroatoms selected from N, O and S, R' represents H, a hydrocarbyl group, or a halogenated hydrocarbyl group, wherein at least one carbon atom of the hydrocarbyl group may be further substituted with one or more heteroatoms selected from N, O and S, or any two of R and R' may together form a divalent hydrocarbylene group, wherein at least one carbon atom of the hydrocarbylene group may be further substituted by one or more heteroatoms selected from N, O and S; and

(b) a second component represented by Formula II:

wherein
each R" independently represents F or $CF_3$;
b represents any positive integer, and
Z represents a b-valent organic moiety free of interfering groups; and wherein the first and second compositions are essentially free of any fluoropolymer comprising an interpolymerized monomer unit having a nitrogen-containing cure site.

In yet another aspect, the present invention provides a curable composition comprising:

(a) a catalyst composition preparable by reaction of components comprising a first component represented by Formula I:

wherein
Q+ is a non-interfering organophosphonium, organosulfonium, or organoammonium cation, each R independently represents H, halogen, a hydrocarbyl group or a halogenated hydrocarbyl group, wherein at least one carbon atom of the hydrocarbyl group may be further substituted with one or more heteroatoms selected from N, O and S, R' represents H, a hydrocarbyl group, or a halogenated hydrocarbyl group, wherein at least one carbon atom of the hydrocarbyl group may be further substituted with one or more heteroatoms selected from N, O and S, or any two of R and R' may together form a divalent hydrocarbylene group, wherein at least one carbon atom of the hydrocarbylene group may be further substituted by one or more heteroatoms selected from N, O and S; and (b) a second component represented by Formula II:

wherein
each R" independently represents F or $CF_3$;
b represents any positive integer;
Z represents a b-valent organic moiety free of interfering groups, and wherein the first and second compositions are essentially free of any fluoropolymer comprising an interpolymerized monomer unit having a nitrogen-containing cure site; and (c) a fluoropolymer comprising at least one interpolymerized monomer unit having a nitrogen-containing cure site.

In yet another aspect, the present invention provides a method of making a fluoroelastomer composition, the method comprising combining:

(a) a first component represented by Formula I:

wherein
Q+ is a non-interfering organophosphonium, organosulfonium, or organoammonium cation;

each R independently represents H, halogen, a hydrocarbyl group or a halogenated hydrocarbyl group, wherein at least one carbon atom of the hydrocarbyl group may be further substituted with one or more heteroatoms selected from N, O and S;

R' represents H, a hydrocarbyl group, or a halogenated hydrocarbyl group, wherein at least one carbon atom of the hydrocarbyl group may be further substituted with one or more heteroatoms selected from N, O and S;

or any two of R and R' may together form a divalent hydrocarbylene group, wherein at least one carbon atom of the hydrocarbylene group may be further substituted by one or more heteroatoms selected from N, O and S;

(b) a second component represented by Formula II:

wherein each R" independently represents F or $CF_3$;

b represents any positive integer;

Z represents a b-valent organic moiety free of interfering groups, and wherein neither of the first and second components are fluoropolymers that comprise an interpolymerized monomer unit having a nitrogen-containing cure site; and (c) a fluoropolymer comprising at least one interpolymerized monomer unit having a nitrogen-containing cure site thereby forming a curable composition; and (d) at least partially curing the curable composition to form a fluoroelastomer.

Methods of making fluoroelastomer compositions according to the present invention typically exhibit a low degree of scorch as compared to prior methods that utilize the first component alone.

Catalysts according to the present invention are useful in methods of making fluoroelastomer compositions according to the present invention.

As used herein, the term

"essentially free of" means containing less than one percent by weight of;

"fluoropolymer" refers to a polymer having a fluorine content of at least 30 percent by weight, based on the total weight of the fluoropolymer;

"hydrocarbyl" refers to a univalent group formed by removing a hydrogen atom from a hydrocarbon;

"hydrocarbylene" refers to a divalent group formed by removing two hydrogen atoms from a hydrocarbon, the free valencies of which are not engaged in a double bond;

"monomer" refers to a molecule that can undergo polymerization thereby contributing constitutional units to the essential structure of an oligomer or polymer, or a substance composed of such molecules;

"monomer unit" refers to the largest constitutional unit contributed by a single monomer molecule to the structure of a polymer;

"nitrogen-containing cure site" refers to a nitrogen-containing group capable of participating in a cure. This can include cure by self-condensation into a triazine structure or curing through the use of curatives such as bis-aminophenols, or via free radical cure mechanisms; and "polymer" refers to a macromolecule formed by the chemical union of at least ten identical combining units called monomers, or a substance composed of such macromolecules.

DETAILED DESCRIPTION

Figure 1:
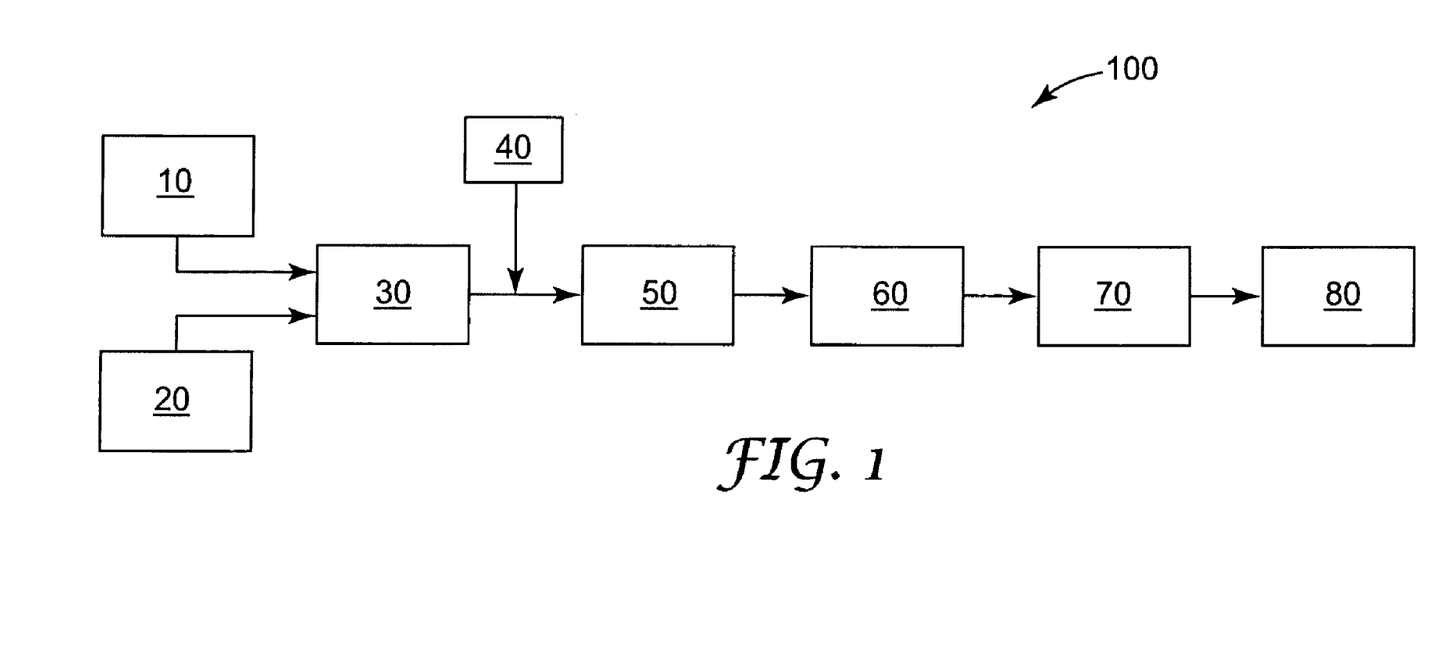
FIG. 1 is a process flow diagram showing an exemplary method for making a shaped fluoroelastomer composition.

An exemplary embodiment of the present invention is shown in FIG. 1, which depicts method 100 for making a shaped fluoroelastomer composition. In practice of method 100, first composition 10 is combined with second composition 20 to form a reaction product 30. Reaction product 30, which comprises a catalyst, is then combined with fluoropolymer 40 having nitrogen-containing cure site components to form curable composition 50. Curable composition 50 is then shaped to form shaped curable composition 60. Shaped curable composition 60 is then at least partially cured to form fluoroelastomer composition 70, which may be optionally post-cured to form post-cured fluoroelastomer composition 80.

The first composition comprises a first component represented by Formula I:

$Q^+$ is a non-interfering organophosphonium, organosulfonium, or organoammonium cation. By the term "non-interfering" it is meant that choices of Q+, which either react with the anionic portion of the first component or interfere with the curing process are excluded. Examples of Q+ include tetrahydrocarbylammonium such as for example, tributylbenzylammonium, tetrabutylammonium, and dibutyldiphenylammonium; tetrahydrocarbylphosphonium such as, for example, triphenylbenzylphosphonium, tetrabutylphosphonium, and tributylallylphosphonium; tributyl-2-methoxypropylphosphonium; trihydrocarbylsulfonium such as for example, triphenylsulfonium and tritolylsulfonium; and heteroatom substituted organophosphonium, organosulfonium, or organoammonium cations such as, for example, benzyl tris(dimethylamino)phosphonium or benzyl(diethylamino)diphenylphosphonium.

Each R independently represents H, halogen, a hydrocarbyl group or a halogenated hydrocarbyl group, wherein at least one carbon atom of the hydrocarbyl group may be further substituted with one or more heteroatoms selected from N, O and S.

For example, R may be H, F, Cl, Br, I, $C_1$-$C_{12}$ alkyl (e.g., methyl, ethyl, hexyl, isooctyl, and isopropyl), $C_6$-$C_{14}$ aryl (e.g., phenyl, naphthyl, biphenylyl, and phenanthryl), $C_7$-$C_{18}$ alkaryl (e.g., toluyl, isodecylphenyl, and isopropylphenyl), $C_7$-$C_{18}$ aralkyl (e.g., phenylmethyl, phenethyl, and phenylpropyl), $C_6$-$C_8$ cycloalkyl groups (e.g., cyclohexyl, norbornyl, and [2.2.2]bicyclooctyl), $C_2$-$C_{12}$ alkoxyalkyl (e.g., methoxymethyl, methoxypropyl) and alkoxyalkoxyalkyl (e.g., methoxymethoxymethyl, ethoxyethoxyethyl, and methoxyethoxyethyl), $C_4$-$C_6$ heteroaryl (e.g., pyridinyl, and pyrazinyl), and partially or perfluorinated derivatives of any of the foregoing.

In some embodiments, R' represents H or an alkyl, aryl, alkaryl, aralkyl, or cycloalkyl group, or a halogenated derivative thereof, wherein a portion of the carbon atoms may be substituted by heteroatoms selected from N, O, and S.

For example, R' may be H, $C_1$-$C_{12}$ alkyl (e.g., methyl, ethyl, hexyl, isooctyl, and isopropyl), $C_6$-$C_{14}$ aryl (e.g., phenyl, naphthyl, biphenylyl, and phenanthryl), $C_7$-$C_{18}$ alkaryl (e.g., toluyl, isodecylphenyl, and isopropylphenyl), $C_7$-$C_{18}$ aralkyl (e.g., phenylmethyl, phenethyl, and phenylpropyl), $C_6$-$C_8$ cycloalkyl groups (e.g., cyclohexyl, norbornyl, and [2.2.2]bicyclooctanyl), $C_2$-$C_{12}$ alkoxyalkyl (e.g., methoxymethyl, methoxypropyl) and alkoxyalkoxylalkyl (e.g., methoxymethoxymethyl, ethoxyethoxyethyl, and methoxyethoxyethyl), $C_4$-$C_6$ heteroaryl (e.g., pyridinyl, and pyrazinyl), and partially or perfluorinated derivatives of any of the foregoing.

In some embodiments, or any two of R and R' may together form a divalent hydrocarbylene group, wherein at least one carbon atom of the hydrocarbylene group may be further substituted by one or more heteroatoms selected from N, O, and S. For example, any two of the R and R' groups may together form a divalent alkylene (e.g., ethylene, propylene, or butylene), arylene, alkarylene, aralkylene or cycloalkylene group wherein a portion of the carbon atoms may be substituted by heteroatoms selected from N, O and S.

In some embodiments, each R is F and R' is selected from H, phenyl, methoxyphenyl, toluyl, phenoxy, fluorophenyl, trifluoromethylphenyl, and $CF_3$.

Specific examples of the first component include tetraalkylammonium 2-phenyl-1,1,1,3,3,3-hexafluoroisopropanoate, tetra-alkylammonium 1,1,1,3,3,3-hexafluoroisopropanoate, tetrabutylphosphonium 2-phenyl-1,1,1,3,3,3-hexafluoroisopropanoate, tetrabutylphosphonium 1,1,1,3,3,3-hexafluoroisopropanoate, tetrabutylphosphonium 2-methoxyphenyl-1,1,1,3,3,3-hexafluoroisopropanoate, and tetrabutylphosphonium 2-p-toluyl-1,1,1,3,3,3-hexafluoroisopropanoate.

The first component can be provided in the first composition in any form such as, for example, as a salt or as a solution of the first component dissolved in a solvent. If in solvent, the solvent should be non-interfering (i.e., it does not react with the first or second components, their reaction product, or the fluoropolymer used to form the fluoroelastomer composition).

Methods for making the first component fluorinated alkoxides are described, for example, in U.S. patent application Ser. No. 11/014,042 (Grootaert et al.), filed Dec. 16, 2004, the disclosure of which is incorporated herein by reference. The second composition comprises a second component represented by Formula II:

(II)

wherein, each R" independently represents F or $CF_3$, b represents any positive integer, and Z represents a b-valent organic moiety free of interfering groups. By the term "free of interfering groups" it is meant that choices of Z that interfere with the reaction of the first component with the second component, or interfere with the curing process, are excluded.

In some embodiments, b is 1, 2, or 3.

In some embodiments, Z is selected from hydrocarbyl, halogenated hydrocarbyl, hydrocarbylene, halogenated hydrocarbylene, —O—,

—S—, and combinations thereof. For example, Z may be perfluorinated hydrocarbyl, perfluorinated hydrocarbylene, —O—, —S—, and combinations thereof. For example, Z may be $C_1$-$C_{12}$ alkyl (e.g., methyl, ethyl, hexyl, isooctyl, and isopropyl), $C_6$-$C_{14}$ aryl (e.g., phenyl, naphthyl, biphenylyl, and phenanthryl), $C_7$-$C_{18}$ alkaryl (e.g., toluyl, isodecylphenyl, and isopropylphenyl), $C_7$-$C_{18}$ aralkyl (e.g., phenylmethyl, phenethyl, and phenylpropyl), $C_6$-$C_8$ cycloalkyl groups (e.g., cyclohexyl, norbornyl, and [2.2.2]bicyclooctanyl), $C_2$-$C_{12}$ alkoxyalkyl (e.g., methoxymethyl, methoxypropyl) and alkoxyalkoxylalkyl (e.g., methoxymethoxymethyl, ethoxyethoxyethyl, and methoxyethoxyethyl), $C_4$-$C_6$ heteroaryl (e.g., pyridinyl, and pyrazinyl), or a partially or perfluorinated derivative of any of the foregoing.

In order to minimize the amount of reaction product of the first and second components that must be included in the curable composition in order to achieve a desired level of cure, the second component should typically be selected such that the equivalent weight is relatively low. For example, the equivalent weight of the second component may be less than 500, 400, or even less than 250 grams per equivalent.

The reaction product of the first and second components may be prepared by other synthetic routes, although the method described above is typically the most direct method. For example, a first species represented by the formula:

wherein $M^+$ is an alkali metal cation (e.g., lithium, sodium, or potassium) or an alkaline earth cation (e.g., magnesium, calcium, or barium) and R and R' are as previously defined; and the second component may be allowed to react, followed by ion exchange or metathesis to replace $M^+$ with $Q^+$.

The second component may be provided in any form such as, for example, as a liquid or as a solution of the second component dissolved in a solvent. If in solvent, the solvent should be non-interfering (i.e., it does not react with the first or second components, their reaction product, or the fluoropolymer used to form the fluoroelastomer composition). A wide variety of nitriles are available commercially or known in the chemical literature. In the case of fluorinated nitriles, which may be desirable in many instances, they may be prepared from the corresponding acid fluorides via subsequent conversion through esters and then amides. The acid fluorides may be prepared by direct fluorination or electrochemical fluorination. For secondary nitriles the acid fluorides may be prepared via hexafluoropropylene (HFPO) coupling. The acid fluorides may be converted to esters via reaction with an appropriate alcohol (such as methanol). The esters may be subsequently converted to the amides via reaction with ammonia. The amides may be dehydrated to the nitriles in an appropriate solvent (such as DMF) with pyridine and trifluoroacetic anhydride. Alternatively the amides may be dehydrated with other reagents such as $P_2O_5$ or $PCl_3$.

Without wishing to be bound by theory, it is believed that combining the first and second components, under conditions such that they mutually react, results in formation of a catalyst composition. The catalyst composition may contain a single component, but more typically contains a mixture of component species that may include at least one of 1:1, 1:2, 1:3, or even higher adducts of the first component with the second component, respectively. Additionally, condensation products of the second component may also be present.

For example, adducts of the first component with the second component may be represented by the formula:

wherein y is any integer greater than or equal to 0 (e.g., 0, 1, 2, or 3), and R, R', R", $Q^+$, b, and Z are as previously defined.

The first and second components may spontaneously react, for example, as evidenced by an exotherm, or a degree of heating may be necessary in order to induce reaction. Accordingly, in some embodiments, the first and second components may be reacted to form a reaction product and then combined with a fluoropolymer having nitrogen-containing cure sites. In other embodiments such as, for example, those embodiments wherein the first and second components do not react at ambient temperatures, the first and second components and a fluoropolymer having nitrogen-containing cure sites may be combined to form a curable composition that, upon heating, forms a reaction product of the first and second components at a temperature below that wherein significant curing takes place. In such embodiments, the reaction product may then effect curing upon further heating to the curing temperature.

In either case, the reaction between the first and second components involves conversion of at least one cyano group of the second component to another chemical form as it is observed by infrared spectroscopy that the cyano group band in the infrared spectrum at least partially disappears (depending on the reaction stoichiometry) upon reaction of the first and second components.

In some embodiments, it may be desirable to control the equivalent ratio of alkoxide to nitrile that are combined. For example, the equivalent ratio of alkoxide to nitrile that are combined may be at least 1:1, 2:1, 3:1, 5:1, or even higher, although other ratios may also be used.

In order to preserve the pot life of the resultant reaction product (i.e., catalyst composition), the first and second compositions may be essentially free of any fluoropolymer comprising nitrogen-containing cure sites, whether in pendant groups, end groups, or both. For example, the first and second compositions may be essentially free of any fluoropolymer comprising an interpolymerized monomer unit having a nitrogen-containing cure site.

If desired, the reaction product of the first and second components may be combined with a fluoropolymer having nitrogen-containing cure sites, thereby forming a curable composition.

Suitable fluoropolymers having nitrogen-containing cure sites typically comprise interpolymerized monomer units derived from a nitrogen-containing cure site monomer and at least one, more typically at least two, principal monomers. Examples of suitable principal monomers include perfluoroolefins (e.g., tetrafluoroethylene (TFE) and hexafluoropropylene (HFP)), chlorotrifluoroethylene (CTFE), perfluorovinyl ethers (e.g., perfluoroalkyl vinyl ethers and perfluoroalkoxy vinyl ethers), and optionally, hydrogen-containing monomers such as olefins (e.g., ethylene, propylene), and vinylidene fluoride (VDF). Such fluoropolymers include, for example, those referred to in the art as "fluoroelastomer gums" and "perfluoroelastomer gums".

In some embodiments, the fluoropolymer comprises interpolymerized monomer units derived from tetrafluoroethylene (TFE), chlorotrifluoroethylene (CTFE), and/or one or more ethylenically-unsaturated monomers represented by the formulas $CF_2=CF-R_f^1$, $CF_2=CF-O-R_f^2$, and $CH_2=CR^3{}_2$, wherein $R_f^1$ is a perfluoroalkyl; $R_f^2$ is a perfluoroalkyl, or a perfluoroalkoxy; and each $R^3$ is independently selected from H, F, Cl, Br, I, or an aliphatic group. In some embodiments, the perfluoroalkyl, perfluoroalkoxy, and aliphatic groups have F, Br, I, and/or or Cl substituents.

In some embodiments, the fluoropolymer comprises at least two interpolymerized monomer units derived from tetrafluoroethylene and at least one of a perfluorinated alkyl vinyl ether, perfluorinated alkoxyalkyl vinyl ether, perfluorinated alkenyl vinyl ether, or perfluorinated alkoxyalkenyl vinyl ether, respectively.

If the fluoropolymer is not perfluorinated, it may contain from about 5 to about 90 mole percent of its interpolymerized monomer units derived from TFE, CTFE, and/or HFP, from about 5 to about 90 mole percent of its interpolymerized monomer units derived from VDF, ethylene, and/or propylene, up to about 40 mole percent of its interpolymerized monomer units derived from a vinyl ether, and from about 0.1 to about 5 mole percent (e.g., from about 0.3 to about 2 mole percent) of a nitrogen-containing cure site monomer.

In some embodiments, the fluoropolymer comprises interpolymerized monomer units corresponding to fluorinated monomers having the formula $CF_2=CF-R_f$, wherein $R_f$ is fluorine or a $C_1$-$C_8$ perfluoroalkyl, and hydrogen-containing $C_2$-$C_9$ olefins, which have less than half of the hydrogen atoms substituted with fluorine, for example less than one-fourth of the hydrogen atoms substituted with fluorine. In some embodiments, the non-fluorinated olefin is absent.

In some embodiments, the fluoropolymer contains at least 50 mole percent of its interpolymerized monomer units derived from TFE and/or CTFE, optionally including HFP. In such embodiments, the balance of the interpolymerized monomer units of the fluoropolymer (10 to 50 mole percent)

is typically be made up of one or more perfluoro vinyl ethers and a nitrogen-containing cure site (e.g., introduced via copolymerization of a cyano group-containing vinyl ether, or by post treatment of pf —CN cure sites after the polymerization by reacting the polymer with alcohols thereby transforming the —CN cure sites into C-alkoxycarbonimidoyl (i.e., —C(=NH)—OR$^5$ wherein R$^5$=alkyl) cure sites). The cure site monomer typically makes up from about 0.1 to about 5 mole percent (more typically from about 0.3 to about 2 mole percent) of the fluoropolymer.

Hydrogen-containing olefins useful in the invention include those of the formula $CX_2$=CX—R$^6$, wherein each X is, independently, hydrogen or fluorine or chlorine, R$^6$ is hydrogen, fluorine, or a $C_1$-$C_{12}$ alkyl. Useful olefins include, for example, partially-fluorinated monomers (e.g., vinylidene fluoride) or hydrogen-containing monomers such as olefins including α-olefins (e.g., ethylene, propylene, butene, pentene, or hexane). Combinations of the above-mentioned materials are also useful.

In some embodiments, the fluoropolymer comprises interpolymerized monomer units derived from tetrafluoroethylene, a fluorinated comonomer, and optionally one or more perfluorovinyl ethers. The fluorinated comonomer may be selected from perfluoroolefins, partially-fluorinated olefins, non-fluorinated olefins, vinylidene fluoride, and combinations thereof. Useful perfluorinated vinyl ethers include, for example, those described in U. S. Pat. Nos. 6,255,536 and 6,294,627 (Worm et al.). Examples include $CF_2$=$CFOCF_3$, $CF_2$=CF—O—$CF_2$—O—$CF_3$, $CF_2$=CF—O—$CF_2$—O—$CF_2CF_3$, $CF_2$=CF——$CF_2$—O—$CF_2CF_2CF_3$, $CF_2$=$CFOCF_2CF_2OCF_3$, $CF_2$=$CFOCF_2CF_2CF_2OCF_3$, $CF_2$=$CFOCF_2CF_2CF_3$, $CF_2$=CF—O—$CF_2CF(CF_3)$—O—$CF_3$, $CF_2$=$CFOCF_2CF(CF_3)OCF_2CF_2CF_3$, $CF_2$=CF—O—$CF_3CF_2$—O—$CF_2$—O—$CF_2$—O—$CF_3$, and $CF_2$=$CFOCF_2CF(CF_3)OCF_2CF(CF_3)OCF_2CF_2CF_3$.

Nitrogen-containing cure sites enable curing the fluoropolymer to form the fluoroelastomer composition. Examples of monomers comprising nitrogen-containing groups useful in preparing fluoropolymers comprising a nitrogen-containing cure site include free-radically polymerizable nitriles, imidates, amidines, amides, imides, and amine-oxides.

Useful perfluorinated vinyl ethers that have nitrogen-containing cure sites include, for example, perfluoro(8-cyano-5-methyl-3,6-dioxa-1-octene); $CF_2$=$CFO(CF_2)_L$CN wherein L is an integer in a range of from 2 to 12, inclusive; $CF_2$=$CFO(CF_2)_u OCF(CF_3)$CN wherein u is an integer in a range of from 2 to 6, inclusive; $CF_2$=$CFO[CF_2CF(CF_3)O]_q (CF_2O)_y CF(CF_3)$CN wherein q is an integer in a range of from 0 to 4, inclusive, and r is an integer in a range of from 0 to 6, inclusive; or $CF_2$=$CF[OCF_2CF(CF_3)]_r O(CF_2)_t$CN wherein r is 1 or 2, and t is an integer in a range of from 1 to 4, inclusive; and derivatives and combinations of the foregoing.

The amount of nitrogen-containing cure sites in a side chain position of the fluoropolymer generally is from about 0.05 to about 5 mole percent (more preferably from 0.1 to 2 mole percent).

Generally, the effective amount of curative, which may include more than one composition, is at least about 0.1 parts curative per hundred parts of the curable composition on a weight basis, more typically at least about 0.5 parts curative per hundred parts of the curable composition. On a weight basis, the effective amount of curative is typically below about 10 parts curative per hundred parts of the curable composition, more typically below about 5 parts curative per hundred parts of the curable composition, although higher and lower amounts of curative may also be used.

The curable composition curing may contain additional curatives such as, for example, those known in the art for curing fluoroelastomer gums, and which should typically be selected so that they do not negatively impact the curing properties of the curable composition. Examples of such additional curative include bis-aminophenols compounds (e.g., see U.S. Pat. No. 5,767,204 (Iwa et al.) and U.S. Pat. No. 5,700,879 (Yamamoto et al.)), organometallic compounds (e.g., see U.S. Pat. No. 4,281,092 (Breazeale)), bis-amidooximes (e.g., see U.S. Pat. No. 5,621,145 (Saito et al.)), ammonia generating compounds (e.g., see U.S. Pat. No. 6,281,296 (MacLachlan et al.), ammonium salts (e.g., see U.S. Pat. No. 5,565,512 (Saito et al.), and amidines (e.g., see U.S. Pat. No. 6,846,880 (Grootaert et al.)), peroxides, and coagents.

One or more additional fluoropolymers may be combined with the fluoropolymer having interpolymerized monomer units derived from a nitrogen-containing cure site monomer. The additional fluoropolymers may, or may not, comprise nitrogen-containing cure sites, and include the entire array described above, and including homopolymers and copolymers comprising the interpolymerized monomer units mentioned above.

The fluoropolymer comprising a nitrogen-containing cure site (e.g., a cyano or imidate group), and any optional additional fluoropolymer(s) that may be incorporated in to the curable composition, may be prepared by methods including, for example, free-radical polymerization of the monomers as an aqueous emulsion polymerization or as a solution polymerization in an organic solvent. Emulsion polymerization typically involves polymerizing monomers in an aqueous medium in the presence of an inorganic free-radical initiator system, such as ammonium persulfate or potassium permanganate, and a surfactant or suspending agent.

Solvent polymerization is typically done in non-telogenic organic solvents, for example, haloperfluoro or perfluoro liquids. Any soluble radical initiator can be used, for example AIBN and bis(perfluoroacyl) peroxides. The polymerization is typically run at a temperature in the range of 25-80° C. and at a pressure in the range of 2-15 bar (0.3-1.5 MPa).

Cyano groups (i.e., —CN) can typically be introduced through selected chain transfer agents like I(CF2)$_d$CN, or by using a free-radical polymerization process can also be carried out in the presence of a perfluorosulfinate such as NC(CF$_2$)$_d$SO$_2$G, where in the two preceding formulas d is an integer from 1 to 10, more typically 1 to 6, and wherein G represents a hydrogen atom or a cation with valence of 1 or 2.

Imidate groups (e.g., —C(=NH)O-alkyl) may be introduced by converting cyano groups in selected polymers into imidate groups. One conversion route of cyano group-containing fluoropolymers involves the reaction of nitriles in the presence of an alcohol component and a base component at ambient temperatures. Alkyl alcohols having from 1 to 10 carbon atoms, which may be partially fluorinated, and combinations of more than one such material can be used for the alcohol component. The corresponding salt(s) of the selected alcohol or amines are preferred for the base component. Further details may be found, for example, in U.S. Pat. No. 6,803,425 (Hintzer et al.), the disclosure of which is incorporated herein by reference.

If the fluoropolymer comprising at least one interpolymerized monomer unit having a nitrogen-containing cure site comprises a perfluoroelastomer, then at least one swelling agent may be added to the polymer(s) prior to curing. Such swelling agent(s) may be a partially fluorinated compound such as a hydrofluoroether (HFE), (e.g., available under the trade designations "3M NOVEC ENGINEERED FLUID HFE-7100" or "3M NOVEC ENGINEERED FLUID HFE-7200" from 3M Company), or any other fluorine containing liquid such as, for example, that available under the trade designation "3M FLUORINERT LIQUID FC-75" from 3M. The conversion of the polymer pendant cyano groups is typically performed at room temperature or at a slightly higher temperature. In general, any fluorine containing inert liquid or any fluorine containing alkanol with a boiling point of at least about 40° C., typically at least about 50° C. may be used.

In the case of non-perfluorinated elastomers, a swelling agent also may be used. Exemplary swelling agents include alcohols, inert hydrocarbon solvents, and fluorinated compounds. The necessary bases are preferably selected from alkoxides or organic amines, e.g., sodium methylate or ethylate, trialkylamines, aryl-containing trialkylamines, and pyridine. The amount of base necessary to convert the nitrites is typically from 0.05-10 weight percent based on the weight of polymer, more typically 0.1-5 weight percent.

If blends of fluoropolymers are desired, one useful route of incorporation is typically through blending the fluoropolymer latices in the selected ratio, followed by coagulation and drying.

Additives such as, for example, carbon black, stabilizers, plasticizers, lubricants, fillers including silica and fluoropolymer fillers (e.g., PTFE and/or PFA (perfluoroalkoxy) fillers), and processing aids typically utilized in fluoropolymer compounding may be incorporated into the compositions, provided that they have adequate stability for the intended service conditions and do not substantially interfere with curing of the curable composition.

The curable composition can typically be prepared by mixing one or more fluoropolymer(s), the catalyst, any selected additive or additives, any additional curatives (if desired), and any other adjuvants (if desired) in conventional rubber processing equipment. The desired amounts of compounding ingredients and other conventional adjuvants or ingredients can be added to the curable composition and intimately admixed or compounded therewith by employing any of the usual rubber mixing devices such as internal mixers, (e.g., Banbury mixers), roll mills, or any other convenient mixing device. The temperature of the mixture during the mixing process typically is kept safely below the curing temperature of the composition. Thus, the temperature typically should not rise above about 120° C. During mixing, it generally is desirable to distribute the components and adjuvants uniformly throughout the gum.

The curable composition is then shaped, for example, by extrusion (e.g., into the shape of a film, tube, or hose) or by molding (e.g., in the form of sheet, gasket, or an O-ring). The shaped article is then typically heated to at least cure the fluoropolymer composition and form a useful article.

Surprisingly, it is discovered that curable compositions according to the present invention typically have an enhanced processing window as compared to corresponding compositions that use equimolar quantities of the corresponding organoonium alkoxide that has not been reacted with a nitrile. This is observed, for example in Mooney scorch times as determined by ASTM D1646-04 "Standard Test Methods for Rubber—Viscosity, Stress Relaxation, and Pre-Vulcanization Characteristics (Mooney Viscometer)", the disclosure of which is incorporated herein by reference. For example, curable compositions according to the present invention may have a Mooney Scorch Time ($t_{18}$) of at least 15 minutes according to ASTM D1646-04.

Molding or press curing of the curable mixture is typically conducted at a temperature sufficient to cure the mixture in a desired time under a suitable pressure. Generally, this is between about 95° C. and about 230° C., preferably between about 150° C. and about 205° C., for a period of from about 1 minute to 15 hours, typically from 5 minutes to 30 minutes. A pressure of between about 700 kPa and about 21,000 kPa is usually imposed on the compounded mixture in a mold. The molds may be first coated with a release agent and baked.

The molded mixture or press-cured article may then, optionally, be post-cured (e.g., in an oven) at a temperature and for a time sufficient to complete the curing, usually between about 150° C. and about 300° C., typically at about 230° C., for a period of from about 2 hours to 50 hours or more, generally increasing with the cross-sectional thickness of the article. For thick sections, the temperature during the post-cure is usually raised gradually from the lower limit of the range to the desired maximum temperature. The maximum temperature used is preferably about 300° C., and this value is held for about 4 hours or more. This post-cure step generally completes the cross-linking and may also release residual volatiles from the cured compositions. Finally, the parts are returned to ambient temperature such as by shutting off the oven heat.

Objects and advantages of this invention are further illustrated by the following non-limiting examples, but the particular materials and amounts thereof recited in these examples, as well as other conditions and, details, should not be construed to unduly limit this invention.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Company, Saint Louis, Mo., or may be synthesized by conventional methods.

These abbreviations are used in the following examples: g=grams, min=minutes, mol=mole; mmol=millimole, phr=parts per hundred parts of rubber, hr=hour, ° C.=5 degrees Celsius, mL=milliliter, L=liter, psi=pounds per square inch, MPa=transform infrared spectroscopy, and N-m=Newton-meter.

The following abbreviations are used throughout the Examples:

| ABBREVIATION | DESCRIPTION |
|---|---|
| TFE | tetrafluoroethylene |
| PMVE | perfluoro(methyl vinyl ether) |
| MV5CN | $CF_2=CFO(CF_2)_5CN$ |
| THI | 2-(p-toluyl)-1,1,1,3,3,3-hexafluoroisopropanol |
| TBPTHI | tetrabutylphosphonium 2-(p-toluyl)-1,1,1,3,3,3-hexafluoroisopropoxide |
| Fluoropolymer A | copolymer of 65.7 mole percent TFE, 33.0 mole percent PMVE and 1.3 mole percent MV5CN made via aqueous emulsion polymerization. |
| SIL1 | silica available under the trade designation "AEROSIL R972" from Degussa AG, Düsseldorf, Germany |
| FIL1 | carbon black available under the trade designation "N-990" from Cabot, Boston, Massachusetts |

Nitrile Preparations

Preparation of Heptafluoro-3-methoxypropanenitrile, $CF_3-O-CF_2CF_2CN$

A 5-L round bottom 3-neck flask equipped with a −78° C. condenser and mechanical stirred was charged with 1025 g of methanol and 300 g of sodium fluoride. 3-Trifluoromethoxytetrafluoropropionyl fluoride (1561 g, 6.7 mol), prepared as described in Example 1 of U.S. Pat. No. 6,482,979 (Hintzer et al.), was added to the flask at −20° C. The reaction mixture was washed with 800 g water and phased split to give 1490 g of methyl-3-trifluoromethoxypropionate for a 91% yield after fractionation. A 5-liter round bottom flask equipped with a mechanical stirrer, a −78° C. condenser and addition funnel was charged with 1463 g of methyl-3-trifluoromethoxypropionate (6 mol) and 940 g of dimethylformamide. The mixture was stirred at room temperature and 125 g of ammonia (7.4 mol) was added to convert the ester to amide. Methanol was vacuum stripped and 1160 g of pyridine (14.7 mol) was added. The mixture was cooled to −14° C. and 1493 g of trifluoroacetic anhydride (7.1 mol) was added. After addition was completed, 1 kg of water was added and the product began to reflux on the condenser. A total of 1165 g of heptafluoro-3-methoxypropanenitrile, $CF_3OCF_2CF_2CN$ was obtained after distillation.

Preparation of the Nitrites: $C_7F_{15}CN$, $CF_3OCF_2CF_2CF_2OCF(CF_3)CN$, and $NCC_4F_8CN$ These nitriles were prepared generally as described in the procedure for $CF_3OCF_2CF_2CN$ above starting with the corresponding acid fluoride, $C_7F_{15}COF$, $CF_3OCF_2CF_2CF_2OCF(CF_3)COF$, and $FCOC_4F_8COF$. The acid fluorides were made by direct fluorination or electrochemical fluorination of the corresponding hydrocarbon analogs as described in U.S. Pat. No. 6,255,536 (Worm et al.).

Alcohol Preparation

Hexafluoro-2-arylisopropanols were prepared generally according to the procedure for making hexafluoro-2-arylisopropanols was followed as described in "Perhalo Ketones. V.1 The Reaction of Perhaloacetones with Aromatic Hydrocarbons", by B. S. Farah et al., Journal of Organic Chemistry (1965), vol. 30, pp. 998-1001.

Preparation of 2-(p-toluyl)-1,1,1,3,3,3-hexafluoroisopropanol (THI), $CH_3C_6H_4C(CF_3)_2OH$ A 600-mL Parr reactor was loaded with 12 g of $AlCl_3$ (0.09 mol, obtained from Fluka Chemika) and 326 g of toluene (3.5mol). The reactor was evacuated and 203 g of hexafluoroacetone (1.22 mol, obtained from SynQuest Laboratories, Inc.) was added over 1.5 hr with stirring at room temperature. The reaction exothermed to 45° C. with a pressure rise up to 49 psi (340 kPa). The reaction was completed after one hour, accompanied by a drop in temperature and pressure. The product mixture was washed twice with 600 ml of water. The organic phase was dried with anhydrous $MgSO_4$, filtered and distilled at 174-176° C. to give 228 g of THI.

Organoonium Preparations

Preparation of Tetrabutylphosphonium 2-(p-toluyl)-1,1,1,3,3,3-hexafluoroisopropoxide (TBPTHI), $CH_3C_6H_4C(CF_3)_2O^-{}^+P(C_4H_9)_4$ A 500-mL round bottom flask equipped with a stir bar was charged with 51 g of THI (0.2 mol) and 42 g of 25 weight percent sodium methoxide in methanol (0.2 mol) was added and heated to a slight methanol reflux. The flask was cooled to room temperature, and a solution of 66 g of tetrabutylphosphonium bromide (0.2 mol) in 66 g of methanol was added. The mixture was heated slightly and stirred for 0.5 hours. The solvent was vacuum stripped and the solid mass was extracted with diethyl ether and the sodium bromide was filtered out. TBPTHI (101 g) was obtained after vacuum stripping the solvent.

Catalyst Preparations

Catalyst A

TBPTHI (3.87 g, 7.5 mmol) was placed in a glass vial. To this viscous, colorless oil was added 0.945 g of $NCCF_2CF_2CF_2CF_2CN$ (perfluoroadipoyl dinitrile, 3.75 mmol) via pipette. The vial was swirled gently at room temperature, and a slight exothermic reaction was observed, with the formation of a yellow viscous oil, which solidified upon standing. The obtained reaction product was dissolved in 5 g of methanol to produce a clear yellow solution. FTIR of Catalyst A (neat sample on KBr plate), compared to the starting TBPTHI, showed the formation of a new chemical compound and the complete loss of the —CN groups during the reaction (absence of peak at ~2260 cm$^{-1}$).

Catalyst B1

TBPTHI (3.87 g, 7.5 mmol) was placed in a glass vial. To this viscous, colorless oil was added 2.45 g of $CF_3OCF_2CF_2CF_2OCF(CF_3)CN$ (7.5 mmol) via pipette. The vial was swirled gently at room temperature. The resulting mixture was dissolved in 5 g of methanol. No indication of a reaction at room temperature was observed.

Catalyst B2

As with catalyst B1, 2.45 g of $CF_3OCF_2CF_2CF_2OCF(CF_3)CN$ and 3.87 g of TBPTHI were combined in a vial in the neat form and no indication of a reaction at room temperature was observed. The vial was then heated at 60° C. resulting in the rapid formation of a bright yellow-orange color which upon shaking and cooling to room temperature transformed the entire contents of the vial to a viscous, oily, yellow-orange substance. FTIR analysis of the neat reaction product (KBr disc), compared to the starting materials used, indicated the —CN function to be completely reacted.

Catalyst C

TBPTHI (3.87 g, 7.5 mmol) was placed in a glass vial. To this viscous, colorless oil was added 2.96 g of $CF_3(CF_2)_6CN$ (7.5 mmol) via pipette. The vial was swirled gently at room temperature, and a slight exothermic reaction was observed, with the formation of a deep yellow viscous oil, which solidified upon standing. The resulting mixture was dissolved in 5 g of methanol.

Catalyst D

TBPTHI (18.6 g, 36 mmol) was charged to a 250-ml round bottom flask equipped with a stir bar and a dry ice condenser. The flask was cooled to 5° C. and 7.6 g (36 mmol) of heptafluoro-3-methoxypropanenitrile was added all at once. A reaction occurred at 10° C. by a change to a yellow colored creamy mixture. The product was warmed to room temperature while maintaining a −78° C. condenser after which the condenser was allowed to warm to room temperature. A yellow creamy paste product, 24.5 g, was recovered.

Catalyst E

Catalyst E was prepared as described for catalyst D except that the molar ratio of heptafluoro-3-methoxypropanenitrile to tetrabutylphosphonium hexafluoro-2-tolylisopropoxide was 2:1 rather than the 1:1 of catalyst D. The actual amounts used were 20 mmol of TBPTHI and 40 mmol of heptafluoro-3-methoxypropanenitrile.

EXAMPLE 1

Fluoropolymer A (300 g) was compounded on a two roll mill with the addition of Catalyst A, SIL1, and FIL1 as indicated in Table 1. The compounded mixture was press-cured at 177° C. for 15 minutes. Subsequently the molded test sheets and O-rings were post-cured in air via a step-post-cure (room temperature to 200° C. over 45 min, hold at 200° C. for 2 hr, ramp to 250° C. over 30 min, hold at 250° C. for 2 hr, ramp to 300° C. over 30 min and hold at 300° C. for 4 hr).

After press-cure and post-cure, physical properties were measured with dumbbells cut from a post-cured test slab.

TABLE 1

| COMPONENT | EX. 1 | EX. 2 | EX. 3 | EX. 4 | EX. 5 | EX. 6 | COMP. EX. A |
|---|---|---|---|---|---|---|---|
| Fluoropolymer A, phr | 100 | 100 | 100 | 100 | 100 | 100 | 100 |
| TBPTHI, phr | 0 | 0 | 0 | 0 | 0 | 0 | 1.3 |
| Catalyst A, phr | 1.6 | 0 | 0 | 0 | 0 | 0 | 0 |
| Catalyst B1, phr | 0 | 2.1 | 0 | 0 | 0 | 0 | 0 |
| Catalyst B2, phr | 0 | 0 | 2.1 | 0 | 0 | 0 | 0 |
| Catalyst C, phr | 0 | 0 | 0 | 2.28 | 0 | 0 | 0 |
| Catalyst D, phr | 0 | 0 | 0 | 0 | 1.82 | 0 | 0 |
| Catalyst E, phr | 0 | 0 | 0 | 0 | 0 | 2.35 | 0 |
| FIL1, phr | 30 | 30 | 30 | 30 | 30 | 30 | 30 |
| SIL1, phr | 1.5 | 1.5 | 1.5 | 1.5 | 1.5 | 1.5 | 1.5 |

Results

Rheology, physical properties, compression set and scorch are shown in Tables 2-5.

Cure rheology tests were carried out using uncured, compounded samples using a rheometer marketed under the trade designation Monsanto Moving Die Rheometer (MDR) Model 2000 by Monsanto Company, Saint Louis, Mo., in accordance with ASTM D 10 5289-93a at 177° C., no pre-heat, 30 minute elapsed time, and a 0.5 degree arc. Both the minimum torque (ML) and highest torque attained during a specified period of time when no plateau or maximum torque was obtained (MH) were measured. Also measured were the time for the torque to increase 2 units above ML ($t_s2$), the time for the torque to reach a value equal to $M_L+0.5(M_H-M_L)$, (t'50), and the time for the torque to reach $M_L+0.9(M_H-M_L)$, (t'90). Results are reported in Table 2 (below).

TABLE 2

| | EX. 1 | EX. 2 | EX. 3 | EX. 4 | EX. 5 | EX. 6 | EX. 6* | COMP. EX. A |
|---|---|---|---|---|---|---|---|---|
| $M_L$, in-lb | 2.15 | 1.62 | 1.15 | 1.54 | 1.34 | 1.15 | 1.79 | 2.08 |
| (N-m) | (0.243) | (0.183) | (0.130) | (0.174) | (0.151) | (0.130) | (0.202) | (0.235) |
| $M_H$, in-lb | 4.38 | 5.13 | 6.93 | 4.97 | 7.92 | 6.12 | 7.37 | 6.36 |
| (N-m) | (0.495) | (0.580) | (0.783) | (0.562) | (0.895) | (0.691) | (0.833) | (0.719) |
| $t_s2$, min | 10.47 | 5.88 | 3.70 | 6.40 | 3.59 | 2.71 | 2.45 | 4.10 |
| t'50, min | 6.15 | 5.29 | 4.93 | 5.67 | 5.14 | 3.17 | 3.13 | 4.35 |
| t'90, min | 10.53 | 9.89 | 9.87 | 10.19 | 9.92 | 8.04 | 7.54 | 9.35 |

*measured after scorch test

EXAMPLES 2-6 AND COMPARATIVE EXAMPLE A

Example 1 was repeated with the substitution of Catalyst B1 (Example 2), B2 (Example 3), C (Example 4) and D (Example 5) and E (Example 6) for Catalyst A as indicated in Table 1 (Below). Comparative Example A used TBPTHI as the catalyst.

Press-cured sheets (150 mm×150 mm×2.0 mm) of the curable compositions prepared in Examples 1-6 and Comparative Example A, except where indicated in Tables 3 and 4, were prepared for physical property determination by pressing at a pressure of about 6.9 MPa and a temperature of 177° C. for 15 min. Press-cured sheets were post-cured by exposure to heat under air using the program detailed in the examples. All specimens were returned to ambient temperature before testing.

Physical Properties

Tensile strength at break, elongation at break, and modulus at 100% elongation were determined according to ASTM D 412-92 using samples cut from the corresponding specimen using ASTM Die D.

Hardness was measured using ASTM D 2240-85 Method A with a Type A-2 Shore Durometer.

Table 3 (below) reports physical properties of the press-cured and post-cured sheets of the curable compositions of Examples 1-6 and Comparative Example A, except where indicated.

TABLE 3

|  | EX. 1 | EX. 2 | EX. 3 | EX. 4 | EX. 5 | EX. 6 | COMP. EX. A |
|---|---|---|---|---|---|---|---|
| Tensile Strength at Break, MPa (psi) | 12.6 (1820) | 12.6 (1830) | nm | 13.7 (1980) | 14.2 (2050) | nm | 12.2 (1770) |
| Elongation at Break, % | 264 | 247 | nm | 205 | 194 | nm | 199 |
| 100% Modulus, MPa (psi) | 8.5 (1200) | 8.2 (1200) | nm | 9.8 (1400) | 12.0 (1700) | nm | 8.9 (1300) |
| Shore A Hardness | 80 | 80 | nm | 80 | 81 | nm | 80 |

In Table 3 (above) "nm" means "not measured"

Specimens of the curable compositions of Examples 1-6 and Comparative Example A, except where indicated in Table 4, were press-cured and post-cured to form O-rings having a cross-section thickness of 0.139 inch (3.5 mm). Compression set of O-ring specimens was measured using ASTM 395-89 Method B. Results are reported in Table 4 (below) as a percentage of permanent set, and were measured at 25% deflection.

TABLE 4

|  | EX. 1 | EX. 2 | EX. 3 | EX. 4 | EX. 5 | EX. 6 | COMP. EX. A |
|---|---|---|---|---|---|---|---|
| Compression set after 72 hr at 316° C., % | 51.1 | 52.8 | nm | 45.8 | 31.9 | nm | 39.8 |

In Table 4 (above) "nm" means "not measured".

Mooney Scorch measurements were made at 121° C., following the procedure described in ASTM D 1646-96. The procedure used employed a one minute preheat, the small rotor size and additionally measured the $t_{10}$ value.

Table 5 (below) reports Mooney scorch test results for curable compositions of Examples 1-6 and Comparative Example A.

In the case of Example 6, after the scorch test was completed, the sample was subjected to rheology tests at 177° C., which indicated excellent cure (see Table 2). This last rheology test indicated that the catalyst was still functional and active after the 61-minute exposure to 121° C. in the compound. The scorch behavior of Example 6 (using Catalyst E) was distinctively different from Example 5 as it showed a very slight initial rise of 3 points, but then remained flat and even came down a bit during the whole scorch test. The scorch curve for Example 5 (using Catalyst D) reached t-18 at 22 minutes, but there was a steady increase in torque due to cure, and after the scorch test the specimen was cured and could not be remolded.

TABLE 5

|  | EX. 1 | EX. 2 | EX. 3 | EX. 4 | EX. 5 | EX.6 | COMP. EX. A |
|---|---|---|---|---|---|---|---|
| Minimum viscosity units | 89.9 | 90.6 | 77.4 | 87.9 | 78.4 | 77.7 | 94.1 |
| t-3 (min) | 5.22 | 3.94 | 11.69 | 5.75 | 10.48 | 12.63 | 4.31 |
| t-10 (min) | 14.4 | 11.55 | 17.79 | 11.71 | 16.58 | >60 | 8.99 |
| t-18 (min) | 26.5 | 16.37 | 30.31 | 17.62 | 22 | >60 | 12.1 |

Various modifications and alterations of this invention may be made by those skilled in the art without departing from the scope and spirit of this invention, and it should be understood that this invention is not to be unduly limited to the illustrative embodiments set forth herein.

What is claimed is:

1. A method of making a fluoroelastomer composition, the method comprising sequentially:
(a) providing a reaction product of first and second compositions, wherein the first composition comprises a first component represented by Formula I:

wherein
Q+ is a non-interfering organophosphonium, organosulfonium, or organoammonium cation;
each R independently represents H, halogen, a hydrocarbyl group or a halogenated hydrocarbyl group, wherein at least one carbon atom of the hydrocarbyl group may be further substituted with one or more heteroatoms selected from N, O and S;
R' represents H, a hydrocarbyl group, or a halogenated hydrocarbyl group, wherein at least one carbon atom of the hydrocarbyl group may be further substituted with one or more heteroatoms selected from N, O and S;
or any two of R and R' may together form a divalent hydrocarbylene group, wherein at least one carbon atom of the hydrocarbylene group may be further substituted by one or more heteroatoms selected from N, O and S; and the second composition comprises a second component represented by Formula II:

$$[N{\equiv}CCFR''{\xrightarrow{\hspace{3mm}}}_b Z] \qquad (II)$$

wherein
each R" independently represents F or CF$_3$;
b represents any positive integer;
Z represents a b-valent organic moiety free of interfering groups; and
(b) combining the reaction product from step (a) with at least one component comprising a fluoropolymer to form a curable composition, the fluoropolymer comprising at least one interpolymerized monomer unit having a nitrogen-containing cure site; and
(c) at least partially curing the curable composition to form a fluoroelastomer.

2. A method according to claim 1, wherein the first and second compositions are essentially free of any fluoropolymer comprising an interpolymerized monomer unit having a nitrogen-containing cure site.

3. A method according to claim 1, wherein at least one of the first or second components is dissolved in solvent.

4. A method according to claim 1, wherein the second component has an equivalent weight of less than or equal to about 500 grams per equivalent.

5. A method according to claim 1, wherein Z represents a b-valent group selected from hydrocarbyl, halogenated hydrocarbyl, hydrocarbylene, halogenated hydrocarbylene, —O—, —S—, and combinations thereof.

6. A method according to claim 1, wherein Z represents a b-valent group selected from perfluorinated hydrocarbyl, perfluorinated hydrocarbylene, —O—, —S—, and combinations thereof.

7. A method according to claim 1, wherein Q$^+$ is selected from the group consisting of tetrahydrocarbylammonium, tetrahydrocarbylphosphonium, and trihydrocarbylsulfonium.

8. A method according to claim 1, wherein each R is F and R' is selected from H, phenyl, methoxyphenyl, toluyl, phenoxy, fluorophenyl, trifluoromethylphenyl, and CF$_3$.

9. A method according to claim 1, wherein the second component is selected from the group consisting of NCCF$_2$CF$_2$CF$_2$CF$_2$CN, CF$_3$OCF$_2$CF$_2$CF$_2$OCF(CF$_3$)CN, CF$_3$(CF$_2$)$_6$CN, CF$_3$OCF$_2$CF$_2$CN, and combinations thereof.

10. A method according to claim 1, wherein at least a portion of the cure sites comprise a cyano group.

11. A method according to claim 1, wherein the fluoropolymer comprises interpolymerized monomer units derived from tetrafluoroethylene and a fluorinated comonomer having a nitrogen-containing cure site.

12. A method according to claim 11, wherein the fluorinated comonomer having a nitrogen-containing cure site comprises a perfluorinated vinyl ether.

13. A method according to claim 12, wherein the perfluorinated vinyl ether comprises perfluoro(8-cyano-5-methyl-3,6-dioxa-1-octene); CF$_2$=CFO(CF$_2$)$_L$CN wherein L is an integer in a range of from 2 to 12, inclusive; CF$_2$=CFO(CF$_2$)$_u$OCF(CF$_3$)CN wherein u is an integer in a range of from 2 to 6, inclusive; CF$_2$=CFO[CF$_2$CF(CF$_3$)O]$_q$(CF$_2$O)$_y$CF(CF$_3$)CN wherein q is an integer in a range of from 0 to 4, inclusive, and r is an integer in a range of from 0 to 6, inclusive; or CF$_2$=CF[OCF$_2$CF(CF$_3$)]$_r$O(CF$_2$)$_t$CN wherein r is 1 or 2, and t is an integer in a range of from 1 to 4, inclusive.

14. A method according to claim 13, wherein the fluoropolymers comprises interpolymerized monomer units selected from perfluoroolefins, partially-fluorinated olefins, non-fluorinated olefins, vinylidene fluoride, and combinations thereof.

15. A method according to claim 1, wherein the fluoropolymer comprises at least two interpolymerized monomer units derived from tetrafluoroethylene and a perfluorinated vinyl ether, respectively.

16. A method according to claim 1, wherein the curable composition has a Mooney scorch time (t$_{18}$) of at least 15 minutes according to ASTM D1646-04.

17. A method according to claim 1, wherein the reaction product of the first and second compositions comprises an adduct of one molecule of the first component with two molecules of the second component.

18. A method according to claim 1, further comprising shaping the curable composition.

19. A shaped fluoroelastomer prepared according to the method of claim 18.

20. A method according to claim 1, further comprising post-curing the fluoroelastomer composition.

21. A method according to claim 1, wherein the at least one component further comprises filler.

22. A method according to claim 20, wherein the filler comprises at least one of fluoropolymer filler, silica, or carbon black.

23. A method according to claim 1, wherein the reaction product comprises at least one component that is a condensation product of one molecule of the first component and two molecules of the second component.

24. A method according to claim 1, wherein the reaction product comprises at least one component that is a condensation product of one molecule of the first component and at least three molecules of the second component.

25. A fluoroelastomer prepared according to the method of claim 1.

26. A curable composition comprising:
(a) first and second components, or a reaction product thereof, wherein the first component is represented by Formula I:

wherein
Q+ is a non-interfering organophosphonium, organosulfonium, or organoammonium cation;

each R independently represents H, halogen, a hydrocarbyl group or a halogenated hydrocarbyl group, wherein at least one carbon atom of the hydrocarbyl group may be further substituted with one or more heteroatoms selected from N, O and S;

R' represents H, a hydrocarbyl group, or a halogenated hydrocarbyl group, wherein at least one carbon atom of the hydrocarbyl group may be further substituted with one or more heteroatoms selected from N, O and S;

or any two of R and R' may together form a divalent hydrocarbylene group, wherein at least one carbon atom of the hydrocarbylene group may be further substituted by one or more heteroatoms selected from N, O and S; and the second component is represented by Formula II:

(II)

wherein each R" independently represents F or $CF_3$;

b represents any positive integer;

Z represents a b-valent organic moiety free of interfering groups, and wherein neither of the first and second components are fluoropolymers that comprise an interpolymerized monomer unit having a nitrogen-containing cure site; and (b) a fluoropolymer comprising at least one interpolymerized monomer unit having a nitrogen-containing cure site.

27. A curable composition according to claim 26, wherein the second component is selected from the group consisting of $NCCF_2CF_2CF_2CF_2CN$, $CF_3OCF_2CF_2CF_2OCF(CF_3)CN$, $CF_3(CF_2)_6CN$, $CF_3OCF_2CF_2CN$, and combinations thereof.

28. A curable composition according to claim 26, wherein the reaction product comprises an adduct of one molecule of the first component with two molecules of the second component.

29. A curable composition according to claim 26, wherein the reaction product comprises at least one component that is a condensation product of one molecule of the first component and at least three molecules of the second component.

30. A curable composition comprising:

(a) a catalyst composition preparable by reaction of components comprising a first component represented by Formula I:

(I)

wherein

Q+ is a non-interfering organophosphonium, organosulfonium, or organoammonium cation, each R independently represents H, halogen, a hydrocarbyl group or a halogenated hydrocarbyl group, wherein at least one carbon atom of the hydrocarbyl group may be further substituted with one or more heteroatoms selected from N, O and S, R' represents H, a hydrocarbyl group, or a halogenated hydrocarbyl group, wherein at least one carbon atom of the hydrocarbyl group may be further substituted with one or more heteroatoms selected from N, O and S, or any two of R and R' may together form a divalent hydrocarbylene group, wherein at least one carbon atom of the hydrocarbylene group may be further substituted by one or more heteroatoms selected from N, O and S; and (b) a second component represented by Formula II:

(II)

wherein each R" independently represents F or $CF_3$;

b represents any positive integer;

Z represents a b-valent organic moiety free of interfering groups, and wherein the first and second compositions are essentially free of any fluoropolymer comprising an interpolymerized monomer unit having a nitrogen-containing cure site; and (c) a fluoropolymer comprising at least one interpolymerized monomer unit having a nitrogen-containing cure site.

31. A curable composition according to claim 30, wherein the catalyst composition is preparable from one equivalent of the first component and two equivalents of the second component.

32. A method of making a fluoroelastomer composition, the method comprising combining:

(a) a first component represented by Formula I:

(I)

wherein

Q+ is a non-interfering organophosphonium, organosulfonium, or organoammonium cation;

each R independently represents H, halogen, a hydrocarbyl group or a halogenated hydrocarbyl group, wherein at least one carbon atom of the hydrocarbyl group may be further substituted with one or more heteroatoms selected from N, O and S;

R' represents H, a hydrocarbyl group, or a halogenated hydrocarbyl group, wherein at least one carbon atom of the hydrocarbyl group may be further substituted with one or more heteroatoms selected from N, O and S;

or any two of R and R' may together form a divalent hydrocarbylene group, wherein at least one carbon atom of the hydrocarbylene group may be further substituted by one or more heteroatoms selected from N, O and S;

(b) a second component represented by Formula II:

(II)

wherein
each R" independently represents F or $CF_3$;
b represents any positive integer;
Z represents a b-valent organic moiety free of interfering groups, and wherein neither of the first and second components are fluoropolymers that comprise an interpolymerized monomer unit having a nitrogen-containing cure site; and (c) a fluoropolymer comprising at least one interpolymerized monomer unit having a nitrogen-containing cure site thereby forming a curable composition; and
(d) at least partially curing the curable composition to form a fluoroelastomer.

* * * * *

UNITED STATES PATENT AND TRADEMARK OFFICE
CERTIFICATE OF CORRECTION

PATENT NO.         : 7,294,677 B2
APPLICATION NO.  : 11/211884
DATED                  : November 13, 2007
INVENTOR(S)         : Werner M. A. Grootaert It is certified that error appears in the above-identified patent and that said Letters Patent is hereby corrected as shown below:

<u>Column 1</u>
Line 20, delete "nitrites" and insert -- nitriles --, therefor.

<u>Column 8</u>
Line 56, delete "nitrites," and insert -- nitriles, --, therefor.
Line 61, delete "nitrites" and insert -- nitriles --, therefor.
Line 67, delete "nitrites" and insert -- nitriles --, therefor.

<u>Column 11</u>
Line 33, delete "$CF_2=CF$" and insert -- $CF_2=CF-O$ --, therefor.
Line 37, delete "$CF_3CF_2$" and insert -- $CF_2CF_2$ --, therefor.

<u>Column 12</u>
Line 56, delete "$I(CF2)_d$" and insert -- $I(CF_2)_d$ --, therefor.

<u>Column 14</u>
Line 67, after "C.=" delete "5".

<u>Column 15</u>
Line 2, delete "Mpa=" and insert -- Mpa= megapascals, FTIR = Fourier --, therefor.
Line 51, delete "Nitrites:" and insert -- Nitriles: --, therefor.

<u>Column 17</u>
Line 36, delete "SILL, and FILL" and insert -- SIL1, and FIL1 --, therefor.

UNITED STATES PATENT AND TRADEMARK OFFICE
CERTIFICATE OF CORRECTION

PATENT NO. : 7,294,677 B2
APPLICATION NO. : 11/211884
DATED : November 13, 2007
INVENTOR(S) : Werner M. A. Grootaert It is certified that error appears in the above-identified patent and that said Letters Patent is hereby corrected as shown below:

Column 18
Line 36, after "ASTM D" delete "10".
Line 38, delete "(ML)" and insert -- ($M_L$) --, therefor.
Line 40, delete "(MH)" and insert -- ($M_H$) --, therefor.
Line 42, delete "ML" and insert -- $M_L$ --, therefor.

Signed and Sealed this

Thirtieth Day of December, 2008

JON W. DUDAS
*Director of the United States Patent and Trademark Office*